United States Patent

Brunke et al.

[11] Patent Number: 5,693,606
[45] Date of Patent: Dec. 2, 1997

[54] ISOLONGIFOLANOL DERIVATIVES, THEIR PRODUCTION AND THEIR USE

[75] Inventors: Ernst Joachim Brunke, Holziminden; Dietmar Schatkowski, Stadtoldendorf, both of Germany

[73] Assignee: DRAGOCO Gerberding & Co. AG, Germany

[21] Appl. No.: 392,044

[22] Filed: Feb. 22, 1995

[30] Foreign Application Priority Data

Feb. 23, 1994 [DE] Germany .................. 44 06 467.5

[51] Int. Cl.⁶ .................................................. A61K 7/46
[52] U.S. Cl. .................. 512/19; 512/14; 568/612; 568/665
[58] Field of Search .................. 568/612, 165; 512/19

[56] References Cited

U.S. PATENT DOCUMENTS

| | | | |
|---|---|---|---|
| 3,647,847 | 3/1972 | Curtis et al. | 260/489 |
| 3,718,698 | 2/1973 | Hall | 260/587 |
| 4,041,084 | 8/1977 | Light et al. | 260/617 F |
| 4,439,354 | 3/1984 | Light et al. | 252/522 R |
| 5,260,459 | 11/1993 | Brunke et al. | 544/336 |
| 5,426,095 | 6/1995 | Brunke et al. | 512/12 |

*Primary Examiner*—Marianne M. Cintins
*Assistant Examiner*—Dwayne C. Jones
*Attorney, Agent, or Firm*—Stein, Pendorf & Van Der Wall

[57] ABSTRACT

The described compounds of the general formula A, in which the wavy lines mean α and β configuration and $R_1$ and $R_2$ mean hydrogen, methyl or ethyl groups

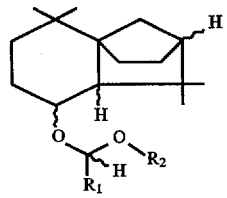

are new and useful as odorants or components or mixtures of odorants or perfume oils. Their production in a method known per se, involves oxidation of isolongifolene obtained from longifolene to isolongifolane, which is then equilibrated with base extraction and/or reduced to isolongifolan-3-ol and this is then reacted with a symmetric acetal of the formula $R_2$—$OCHR_1$—O—$R_2$, in which $R_1$ is hydrogen or methyl and $R_2$ is methyl, ethyl or propyl.

6 Claims, No Drawings

ISOLONGIFOLANOL DERIVATIVES, THEIR PRODUCTION AND THEIR USE

There is a constant demand for olfactory substances having improved characteristics such as olfactory quality, stability in technical applications, skin tolerance and environmental tolerance. For the purpose of ecological balance, products should be aimed for which are based on raw materials which grow again and which after use can easily be biologically degraded. A raw material of natural origin which is available in relatively large quantities is the sesquiterpene longifolen (1) which is present as the main component of Indian oil of turpentine and as a minor component in many other oil of turpentine varieties and other essential oils.

Over two centuries ago, a series of derivatives of longifolene (1) had been produced and certain characteristics as an olfactory substance have been described. G. Ohloff reports in his book "Riechstoffe und Geruchssinn [Olfactory substances and the sense of smell] (Springer Verlag, Berlin 1990, ISBN-No. 3-540-52560-2, pages 87–88), in summary, that at least 4 commercial olfactory substances are produced from longifolen (1) and that 13 olfactory substances are commercially utilised using isolongifolen (2) which is produced starting from longifolen by isomerisation. G. Färber and H. Tan [G. Färber, Parfümerie+Kosmetik, 68, 18, (1987), H. Tan, Parfümerie+Kosmetik, 67, 564 (1986)] reported the chemistry and the olfactory characteristics of the commercially important derivatives of isolongifolen (2). Basically, compared to the similar longifolene-derivatives, the compounds obtained from isolongifolene (2) are sensorily more valuable olfactory substances of a warm-woody olfactory type.

In our own DE-A-41 38 732, cyclic isolongifolanone-ketals of the general Formula B

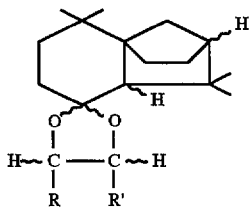

have been described (in which the wavy lines mean the α- and β-configuration and R and R' mean hydrogen- or methyl- or ethyl- groups). These ketals are valuable olfactory substances which have strong woody olfactory characteristics with flowery-fresh effects and a velvet mossy/ambergris character.

Some of the above mentioned olfactory substances are obtained by the following reaction route. Epoxide 3 which is producible by the conversion of isolongifolen (2) with peracids can be converted in a known manner into mixtures of the epimeric ketones 4a/4b. Thereby, these ketone mixtures may show different isomer distribution and olfactory effects depending on the production conditions. Ketone 4a is formed preferentially when the reaction is controlled kinetically whilst ketone 4b is the epimer which is thermodynamically more stable. Compounds 3 and 4a/4b are commercial olfactory substances.

According to the state of the art, this field of olfactory substance chemistry has been particularly well studied. In addition to some longifolene and isolongifolene derivatives having olfactory characteristics, a larger number of derivatives of the named sesquiterpenes are known which either have no or only minimal olfactory value. For this reason it is particularly surprising that now in the field of isolongifolene derivatives the new compounds which are described herein and which are of the Formula A

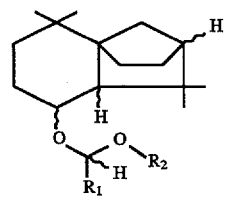

(in which the wavy lines mean α-and β-configurations, and $R_1$ and $R_2$ are hydrogen or methyl or ethyl groups) could be found which have independent olfactory characteristics and which thereby are clearly distinguished from the known olfactory substances derived from isolongifolen (2) and which also surpass these. The isolongifolene-derivatives of the general Formula A have olfactory characteristics of a woody-type and at the same time they give a radiating strong effect which enhances very different perfume notes and prolongs their fragrance effect.

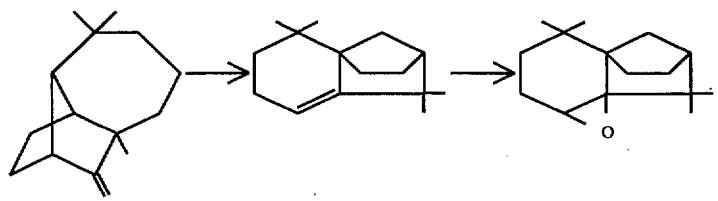

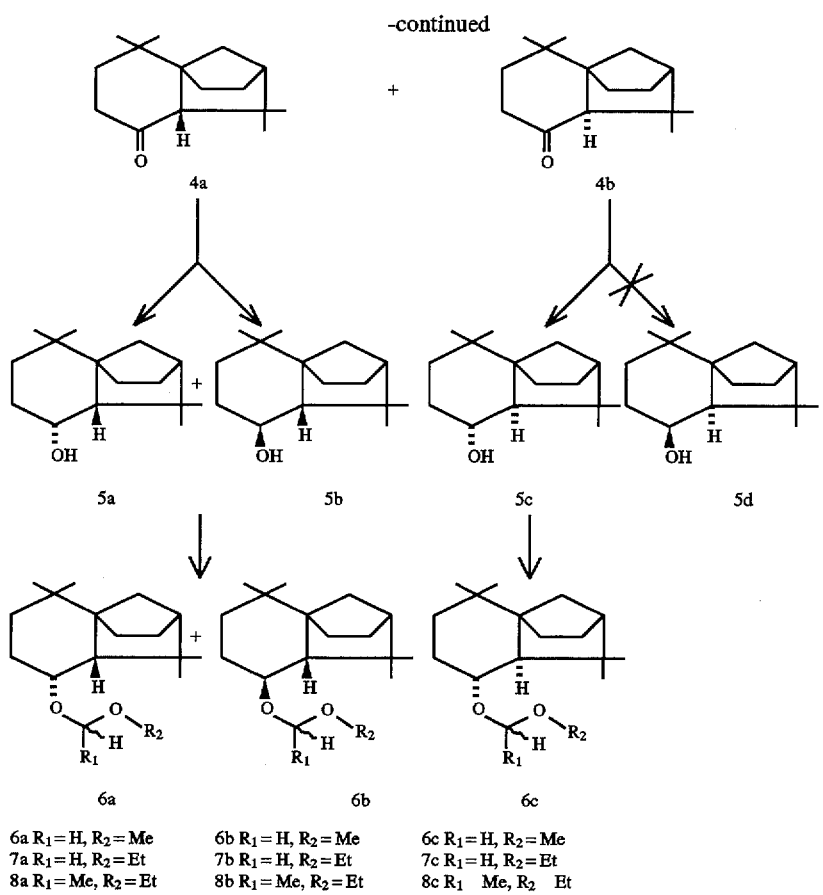

-continued 5a  5b  5c  5d 6a  6b  6c

6a R₁=H, R₂=Me     6b R₁=H, R₂=Me     6c R₁=H, R₂=Me
7a R₁=H, R₂=Et     7b R₁=H, R₂=Et     7c R₁=H, R₂=Et
8a R₁=Me, R₂=Et    8b R₁=Me, R₂=Et    8c R₁ Me, R₂ Et

For the production of compounds of the general Formula A, longifolene (1) was isomerised to isolongifolene (2) in a known manner by treatment with a mixture of acetic acid and sulphuric acid [U. R. Nayak, S. Dev, Tetrahedron, 8, 42–48 (160)] or with boron trifluoride etherate [R. E. Beyler, G. Okrisson, J. Org. Chem., 30, 2838–2839 (1965)]. The epoxide 3 obtained from isolongifolen (2) [L. K. Lala, J. B. Hall, J. Org. Chem., 35, 1172 (1970), I. R. Prahlad, R. Ranganathan, W. R. Nayak, T. S. Santhanakrishnan, S. Dev, Tetrahedron Lett., 8, 417, (1964)] was converted into the mixture of the epimeric ketones 4a/b in a known manner. [R. Ranganathan, W. R. Nayak, T. S. Santhanakrishnan, S. Dev, Tetrahedron, 26, 621 (1970)].

The structural formula was based on the NMR results by J. Bombarda, J. Smadja., E. M., Gaydou., J.-Y. Conan and R. Faure, J. Agric. Food Chem. 42, 136–142 (1994). A ketone mixture 4a/b resulted from ring opening of the epoxide under kinetic control. It has been known that the ketone 4a can be isomerised into the thermodynamically more stable ketone 4b under the influence of basic catalysts or by thermal load. Depending on the reaction conditions, equilibrium mixtures of the ketones 4a/4b are obtained. Ketones 4a and 4b either in a pure form or in a mixture can be converted in a known manner into the epimeric alcohols 5a/b/c [L. K. Lala., J. Org. Chem., 36, 2560–2561 (1971)]. Alcohol 5d has so far not yet been described and also could not be detected during our experiments.

The alcohols 5a/b/c either in a mixture or in their pure form were converted with the symmetrically substituted acetals R₂—O—CHR₁—O—R₂. Thereby the mixed acetals of the formulae 6a/b/c, 7a/b/c or 8a/b/c were obtained either as mixtures or in a pure form. The structural formula revised by J. Bombarda et al. [J. Agric. Food. Chem. 42, 136–142 (1994)] has been adopted for 5a; by analogy the alcohols obtained according to a given protocol were given the structural formulae 5b/5c.

Starting from the ketone 4a, as expected, the thermodynamically more stable ketone 4b was obtained under either base or thermally controlled conditions. Its reduction again did not result in the expected mixture of the epimeric alcohols 5c/5d, but instead merely in the crystalline alcohol 5c. By conversion of 5c with the above mentioned symmetrically substituted acetals, the mixed acetals 6c and 7c were each obtained in a pure form.

The epimeric alcohols 5a and 5b were obtained from isolongifolanone 4a by reduction and they were isolated by chromatographic methods. Conversion with the above mentioned symmetric acetals resulted each in the acetals 6a, 7a and 6b and 7b in a pure form. The characterisation by spectroscopy and the determination of the olfactory characteristics therefore could be performed using pure substances.

Alternatively, a mixture of the ketones 4a/b obtained from isolongifolene-epoxide 3 can be reduced to a mixture of the diastereomeric alcohols 5a/b/c which then result in a mixture of the acetals 6a/b/c or 7a/b/c after conversion with the symmetrical acetals R₂—O—CHR₁—O—R₂. Depending on the chosen reaction conditions, the epimeric ketones 4a and 4b can thereby be produced in differing mass ratios so that after the reduction, the diastereomeric alcohols 5a/b/c are also present in differing mass ratios. During the conversion using the symmetrical acetals R₂—O—CHR₁—O—R₂ the stereochemical ratios essentially remain unchanged so that the new mixed acetals of the Formula A are in this case present as the mixture of diastereomers.

The new mixed acetals of the Formula A either in pure form or as stereoisomer mixtures have original olfactory substance characteristics and either in the pure form or as a diastereomeric mixture they can advantageously be used as olfactory substances or as components of perfume oils.

EXAMPLE 1

Production of isolongifolene (2)

816 g (3.16 mol) of longifolen (1) (80%, from Indian turpentine oil, $[a]_D=39.4°$) were added drop by drop over a 60 minute period to a solution of 360 g toluene and 40 g (0.28 mol) $BF_3$-etherate which had been heated to 60° C. The stirring was continued for 3 hours at 100° C., the mixture was then cooled to room temperature and washed to neutrality using soda solution and water. After drying over $Na_2SO_4$, the solvent was removed by distillation at low pressure. 800 g (74% after GC) of the raw product remained.

Gas chromatogram (Shimadzu GC 14A, DBWAX-30 N, 30 m, 100°–240° C., 10° C./min); $t_R=5.16$ min, 74% 2.

EXAMPLE 2

Production of the isolongifolanone-mixture 4a/b (96:4)

800 g (2.90 mol) of isolongifolene (2) (74% after GC) from Example 1 and 276 g (6 mol) formic acid were introduced into a triple necked flask with reflux cooler and drop funnel and were heated to 60°–70° C. Over a period of one hour, 500 g (5.67 mol) $H_2O_2$ (35%) were then added drop by drop. After 3 hours stirring at 80°–85° C. the mixture was cooled to room temperature and processed. The organic phase was removed and washed to neutrality using soda solution and water, dried over $Na_2SO_4$ and the solvent was removed by distillation at low pressure. 804 g of raw product remained.

GC: 4a (71%); 4b (3.1%) [96:4].

EXAMPLE 3

C-3-epimerisation of isolongifolanone (4a/4b)

220 g (1 mol) of the ketone mixture 4a/b from Example 2, 200 g methanol, 10 g NaOH (0.125 mol) were introduced into a one liter triple necked flask and stirred for a total of 8 hours under reflux. 7.5 g (0.125 mol) glacial acetic acid was then added and the reaction was cooled, the solvent was removed by distillation at low pressure, the residue was resuspended in $H_2O$, 100 g of ether were added and the organic phase was removed. The aqueous phase was then extracted with 100 g ether, the pooled organic phases were washed with soda solution and water, dried over $Na_2SO_4$ and the solvent was removed at low pressure. 212 g of raw product were left as a dark-brown oil.

GC (conditions see Example 1): 4a (6.0%), 4b (69.1%) [8:92].

EXAMPLE 4

Production of the isolongifolanol mixture 5a/b/c 800 g (2.90 mol) isolongifolanone from Example 2 and 400 g methanol were introduced into a triple necked flask with reflux cooler and drop funnel. Over a period of 1 hour and up to a maximum of 50° C., a solution of 250 g water, 4 g NaOH and 37.8 g (1 mol) $NaBH_4$ was then added drop by drop and the mixture was stirred for 4 hours at a temperature of 40° to 50° C. The solvent was then removed by distillation at low pressure, the residues were resuspended in 500 g water and the organic phase was removed. The removed aqueous phases were pooled and extracted with 200 g hexane. The pooled organic phases were washed to neutrality using water, dried over $Na_2SO_4$ and the solvent was removed at low pressure. 768 g of the raw product remained.

GC (conditions see Example 1): 5a (54.9%), 5b (15.3%), 5c (1%)

GC/MS: HP5985 A DBWAX-60 N, 60 m, 60°–240° C., 4° C./min

| | |
|---|---|
| 5a Rt = 38.47 min. | |
| MS(70 eV): m/e(%) = | 222(1, M⁺), 189(100), 161(50), 133 (33), 125(23), 119(38), 105(54), 91 (63), 55(38), 41(53) |
| 5b Rt = 39.12 min. | |
| MS(70 eV): m/e(%) = | 222(42, M⁺), 207(88), 166(54), 151 (66), 123(75), 109(72), 95(67), 81 (62), 55(73), 41(100). |
| 5c Rt = 39.98 min. | |
| MS(70 eV): m/e(%) = | 222(26, M⁺), 207(100), 189(33), 166 (55), 137(34), 123(45), 109(31), 69 (31), 41(49). |

EXAMPLE 5

Production of isolongifolanol 5a 1 g of the raw isolongifolanol 5a/b/c produced in Example 4 was purified using preparative chromatography.

Chromatographic conditions: 150 g silica gel 60, grain size 0.04–0.063 mm (Firm Merck, Article-No. 9385)

| | |
|---|---|
| Solvent: | benzine/acetic acid = 9/1 |
| Initial weight: | 1 g |
| Yield: | 185 mg of colourless crystals GC(conditions see Example 1): 5a(97%) Boiling point: 126–128° C. |
| GC/MS: conditions see Example 4 | |
| 5a Rt = 38.47 min. | |
| MS(70 eV): m/e(%) = | 222(1, M⁺), 189(100), 161(50), 133 (33), 125(23), 119(38), 105(54), 91 (63), 55(38), 41(53). |
| ¹³C-NMR(CDCl₃), Varian VXR-300): | δ [ppm]: 22.07, 23.43 27.57, 32.98(CH₃), 22.67, 25.58, 32.10, 37.91(CH₂), 48.20, 52.17, 68.12(CH), 33.66, 37.65, 54.60(C). |

EXAMPLE 6

Production of isolongifolanol 5c 212 g (0.72 mol) of isolongifolanone from Example 3 and 10 g methanol were introduced into a triple necked flask with reflux cooler and drop funnel. Over a period of 0.5 hours up to a maximum of 50° C., a solution of 70 g water, 1 g NaOH and 9.5 g (0.25 mol) $NaBH_4$ was then added drop by drop and the mixture was further stirred for 3 hours at 40°–50° C. The solvent was then removed by distillation at low pressure, the residue was resuspended in 100 g of water and 100 g of ether, the organic phase was removed, the aqueous phase was again extracted with 100 g ether and the pooled organic phases were washed to neutrality using water, dried over $Na_2SO_4$ and the solvent was removed by distillation at low pressure. 198 g of an oily, solidifying product remained.

GC (conditions see Example 1): 5a (2.1%), 5b (3.1%), 5c (65.1%)

By recrystallising of 100 g of the raw product thus obtained from 200 g of hexane fraction 63/80

53 g 5c were obtained as colourless crystals, boiling point 126°–128° C.

GC (conditions see Example 1): 5c (95.1%).

EXAMPLE 7

Production of a mixture of formaldehyde-methyl-isolongifolanyl acetals (6a/b/c)

111 g (0.36 mol) isolongifolanol from Example 3 [GC: 5a (54.9%), 5b (15.3%), 5c (1%)], 2 g para-toluene sulphonic acid and 228 g (3 mol) formaldehyde dimethyl acetal were introduced into a triple necked flask with a drop funnel, 20 cm glass filling body column and column head and heated to boiling. Over an 8 hour period, a total of 150 g of an azeotropic mixture of methanol/formaldehyde diethyl acetate was then removed by distillation whereby at the same time 152 g (2 mol) formaldehyde dimethyl acetal were added drop by drop over a period of 8 hours. The mixture was then stirred for a further 16 hours under reflux, cooled to room temperature and washed to neutrality using soda solutions and water. 117 g of the raw product remained.

GC (conditions see Example 1): 6a (49.1%), 6b (13.3%), 6c (0.9%)

Distillation using a 15 cm Vigreux-column resulted in 107 g 6a/b/c,
$Bp_{2mm} 120°-150°$ C.

GC (conditions see Example 1): 6a (51.4%), 6b (15.6%), 6c (1.1%).

The fine distillation that followed using a 50 cm metal filling body column resulted in 67 g $bp_{2mm} 135°-139°$ C.

GC (conditions see Example 1): 6a (75.3%), 6b (20.8%), 6c (2.3%).
D 20/4=0.9854
n 20/D=1.4753
$[\alpha]20/D=+2.1°$

EXAMPLE 8

Production of a mixture of formaldehyde-ethyl-isolongifolanyl acetals (7a/b/c)

500 g (1.60 mol) isolongifolanol from Example 3 [GC: 5a (54.9%), 5b (15.3%), 5c (1%)], 5 g para-toluene sulphonic acid and 342 g (3 mol) formaldehyde diethyl acetal were introduced into a triple necked flask with drop funnel, 20 cm glass filling body column with a column head and were heated to boiling. Over a period of 8 hours, a total of 212 g of an azeotropic mixture of ethanol/formaldehyde diethyl acetal was removed by distillation whilst at the same time 208 g (2 mol) of formaldehyde dimethyl acetal were added drop by drop over a period of 8 hours. The reaction mixture was then cooled to room temperature and was washed to neutrality using soda solution and water. 513 g of the raw product remained.

GC (conditions see Example 1): 7a (52.3%), 7b (14.9%), 7c (0.8%)

A distillation using a 15 cm Vigreux column resulted in 493 g of raw 7a/b/c, $bp_{2mm} 115°-158°$ C.

GC (conditions see Example 1): 7a (53.1%), 7b (15.3%), 7c (0.7%)

The fine distillation that followed using a 50 cm metal filling body column resulted in 311 g $bp_{2mm} 141°-144°$ C.

GC (conditions see Example 1): 7a (58.1%), 7b (22.0%), 7c (15.4%)
D20/4=0.9899
n 20/D=1.4867
$[\alpha]20/D=+3.3°$

EXAMPLE 9

Production of formaldehyde-methyl-isolongifolanyl acetal 6c 5 g of the isolongifolanol 5c obtained in Example 5 were converted to 4.95 g of raw formaldehyde-methyl-isolongifolanyl acetal 6c in the manner described in Example 6.

GC (conditions see Example 1): 5c: 21.5%: 6c: 72.8[[]jf44bEXAMPLE 10

Isolation of formaldehyde-methyl-isolongifolanyl acetal 6c 1 g of raw acetal from Example 8 [GC: 6c (72.8%)] were purified using several flash-chromatography separations (2x).

Chromatographic conditions: 200 g silica gel 60, grain size 0.04–0.063 mm (Firm Merck, Article No. 9385)

| Solvent: | Benzine/acetic acid = 98/2 |
|---|---|
| Initial material: | 1 g |
| Yield: | 195 mg |
|  | GC(conditions see Example 1): 6c(89.2%) |
| GC/MS-conditions see Example 4 |  |
| 6c Rt = 37.79 min. |  |
| MS(70 eV): m/e(%) = | 266(20, M⁺), 189(31), 165(33), 109 (56), 107(25), 102(26), 95(43), 81 (34), 69(25), 45(100). |
| $^{13}$C-NMR(CDCl$_3$), Varian VXR-300): | δ [ppm]: 24.85, 25.35, 26.70, 25.66(CH$_3$), 25.35, 28.05, 29.14, 55.66(CH$_3$), 31.16, 36.99, 37.20, 95.81(CH$_2$), 49.27, 57.00, 79.11(CH), 32.25, 40.64(56.29(C). |

EXAMPLE 11

Production of formaldehyde-ethyl-isolongifolanyl acetal 7c 10 g of the isolongifolanol 5 c obtained in Example 5 were converted to 9.8 g of raw formaldehyde-ethyl-isolongifolanyl acetal 7c in the manner described in Example 7.

GC (conditions see Example 1): 5c: 16.6%; 7c: 79.1[[]jf44bEXAMPLE 12

Isolation of formaldehyde-ethyl-isolongifolanyl acetal 7c 1 g of the raw acetal from Example 8 [GC: 7c (79.1%)] were purified using flash-chromatography.

Chromatographic conditions: 150 g silica gel 60, grain size 0.04–0.063 mm (Firm Merck Article No. 9385)

| Solvent: | Benzine/acetic acid = 95/5 |
|---|---|
| Initial material: | 1 g |
| Yield: | 495 mg; GC: 7c(95.1%) |
| GC/MS-conditions see Example 4 |  |
| 7c Rt = 38.39 min. |  |
| MS(70 eV): m/e(%) = | 280(9, M⁺), 204(26), 165(37), 116 (30), 109(55), 95(37), 81(26), 69 (26), 59(100), 31(35). |
| $^{13}$C-NMR(CDCl$_3$), Varian VXR-300): | δ [ppm]: 15.07, 24.87 25.34, 26.71, 29.15(CH$_3$), 26.34, 27.92, 31.17, 36.99, 37.20, 63.56, 94.13(CH$_2$), 49.28, 57.04, 78.80 (CH), 32.28, 40.64, 56.71(C). |

EXAMPLE 13

Isolation of formaldehyde-ethyl-isolongifolanyl acetal mixture 7a/7b 1 g of the raw acetal from Example 7 were purified using preparative gas chromatography.

Chromatographic conditions: GC: G/RA CAP 12, aluminium column Carbowax 10% occupancy, ⅜ inch, 200° C. isothermic; gas flow: 120 ml/min;

Detector: W OL; Injections: 20×50 mg

Yield: 135 mg; GC (conditions see Example 1): 7a (96.1%) 53 mg; GC (conditions see Example 1): 7b (92.0%) GC/MS conditions see Example 4
7a Rt=35.15 min.

| | |
|---|---|
| MS(70 eV): m/e(%) = | 280(7, M$^+$), 204(56), 161(40), 109 (35), 105(40), 91(43), 59(100), 41 (40), 31(46). |
| $^{13}$C-NMR(CDCl$_3$), Varian VXR-300): | δ [ppm]: 15.12, 22.35 26.31, 27.54, 33.08($\underline{C}$H$_3$), 22.51, 25.50, 28.77, 32.80, 37.90, 63.52, 95.44($\underline{C}$H$_2$), 48.35, 52.12, 75.90($\underline{C}$H), 33.52, 37.55, 54.88($\underline{C}$). |
| 7b Rt = 37.22 min. | |
| MS(70 eV): m/e(%) = | 280(7, M$^+$), 204(47), 189(19), 161 (22), 109(35), 95(31), 81(24), 69 (23), 59(100), 31(38). |
| $^{13}$C-NMR(CDCl$_3$), Varian VXR-300): | δ [ppm]: 15.10, 21.16, 23.29, 26.46, 33.27($\underline{C}$H$_3$), 21.53, 26.46, 30.43, 36.48, 27.68, 63.55, 94.70($\underline{C}$H$_2$), 48.36, 53.79, 76.56($\underline{C}$H), 37.47, 56.41($\underline{C}$). |

EXAMPLE 14

Isolation of formaldehyde-methyl-isolongifolanyl acetal 6a 1 g of the mixture of formaldehyde-methyl-isolongifolanyl acetals 6a/b/c obtained in Example 6 was purified by several flash-chromatographic separations (3x).

Chromatographic conditions: 150 g silica gel 60, grain size 0.04–0.063 mm (Firm Merck, Article-No. 9385)

| | |
|---|---|
| Solvent: | Benzine/acetic acid = 95/5 |
| Initial material: | 1 g |
| Yield: | 85 mg |
| | GC(conditions see Example 1): 6a(98%) |
| GC/MS conditions see Example 4 6a Rt = 34.25 min. | |
| MS(70 eV): m/e (%) = | 266(6, M$^+$), 204(47), 189(59), 161 (32), 109(26), 105(32), 91(34), 81 (24), 45(100), 41(24). |
| $^{13}$C-NMR(CDCl$_3$), Varian VXR-300): | δ [ppm]: 22.40, 23.60 27.55, 33.07, 55.70($\underline{C}$H$_3$), 22.05, 25.50, 28.86, 32.82, 37.89, 97.08 ($\underline{C}$H$_2$), 48.34, 52.13, 76.11($\underline{C}$H), 33.50, 37.54, 54.87($\underline{C}$). |

EXAMPLE 15

Isolation of formaldehyde-methyl-isolongifolanyl acetal 6b 3 g of the mixture of formaldehyde-methyl-isolongifolanyl acetals 6a/b/c obtained in Example 6 were purified by several flash-chromatographic separations (3x).

Chromatographic conditions: 300 g silica gel 60, grain size 0.04–0.063 mm (Firm Merck, Article-No. 9385)

| | |
|---|---|
| Solvent: | Benzine/acetic acid = 95/5 |
| Initial material: | 3 g |
| Yield: | 146 mg |
| | GC(conditions see Example 1): 6b (92.3%) |
| GC/MS conditions see Example 4 6b Rt = 36.56 min. | |
| MS(70 eV): m/e (%) = | 266(M$^+$), 81, 234(9), 204(67), 189 (312), 161(30), 109(37), 95(32), 81 (28), 69(20), 45(100). |

| | |
|---|---|
| $^{13}$C-NMR(CDCl$_3$), Varian VXR-300): | δ [ppm]: 21.17, 23.27 26.46, 32.20, 55.70($\underline{C}$H$_3$), 21.52, 26.46, 30.48, 36.48, 37.67, 96.29 ($\underline{C}$H$_2$), 48.61, 53.75, 76.74($\underline{C}$H), 37.44, 56.36($\underline{C}$). |

EXAMPLE 16

Production of a mixture of acetaldehyde-ethyl-isolongifolanyl acetals (8a/b/c)

70.2 g (0.25 mol) isolongifolanol from Example 2 and 1 g of concentrated HCl were introduced into a triple necked flask with reflux cooler and drop funnel. Over a one hour period at 10° C., a solution of 253 g (1.14 mol) of isolongifolanol from Example 2 and 358 g (5.73 mol) of vinyl-ethyl ether were then added drop by drop and the mixture was stirred for 48 hours at room temperature. After this time, the reaction mixture was washed to neutrality once with 100 g of saturated sodium hydrogen carbonate solution and then with water, dried over Na$_2$SO$_4$ and excess vinyl-ethyl-ether was removed at low pressure. 318 g of the raw product remained. A distillation using a 15 cm Vigreux-column resulted in 297 g 8a/b/c, bp$_{2mm}$ 92°–140 ° C. The fine distillation that followed using a 50 cm metal filling body column resulted in 147 g bp$_{2mm}$ 135°–139 ° C.

GC (conditions see Example 1): Σ from 8a/b/c= approximately 92.5%
D20/4=0.9769
n20/D=1.4841
[α]20/D=−5.0° C.
GC/MS conditions see Example 4

| | |
|---|---|
| Rt 33.46 min. MS (70 eV): m/e (%) = | 276 (2), 266 (3), 221 (18), 203 (7), 177 (7), 149 (5), 73 (100), 45 (31), 31 (5). |
| Rt 34.42 min. MS (70 eV): m/e (%) = | 265 (1), 221 (20), 203 (7), 177 (7), 149 (5), 104 (3), 91 (4), 73 (100), 45 (30). |
| Rt 34.76 min. MS (70 eV): m/e (%) = | 279 (1), 265 (1), 121 (2), 205 (10), 149 (3), 109 (3), 95 (4), 73 (100), 45 (24), 41 (4). |
| Rt 36.00 MS (70 eV): m/e (%) = | 265 91), 205 (4), 149 (3), 109 (2), 91 (2), 81 (3), 73 (100), 45 (22). |
| Rt 36.44 MS (70 eV): m/e (%) = | 279 (1), 205 (10), 149 (3), 109 (3), 95 (4), 81 (3), 73 (100), 45 (23). |
| Rt 37.42 min. MS (70 eV): m/e (%) = | 265 (1), 205 (5), 149 (3), 109 (2), 91 (2), 73 (100), 45 (23). |

EXAMPLE 17

Olfactory description of the acetals 6a/b/c to 8a/b/c

The olfactory assessment was performed by a panel of experts using a 10% ethanolic solution and perfume strips.

6a/b/c from Example 7:
woody, spicy, herby, slightly green-metallic, exciting.

6a from Example 14:
woody, powdery, exciting, warm-soft, weaker than 6b, stronger than 6c.

6b from Example 14:
strong, spicy-peppery, strongly woody-fresh, slightly herby-metallic 6c from Example 10:
woody, fennel-note 7a/b/c from Example 8:
strongly woody, agitating, powdery, warm-fruity 7a from Example 13:

acidic-woody, exciting, slightly green-dusty, weaker than 7b, stronger than 7c.

7b from Example 13:
strong, dry-powdery-spicy, green, herby, exciting 7c from Example 12:
woody, herby, sweetish 8a/b/c from Example 16:
woody, dry

EXAMPLE 18

First use example
Perfume oil for an oriental type feminine perfume

By the addition of 20 parts of the compound 7a/7b/7c, the oriental-flowery olfactory character is clearly enhanced. A "lifting" effect is given to the composition and it shows an improved fixation.

| | | |
|---|---|---|
| Orange oil Guinea | 20 | — |
| Aldehyde C14 | 5 | — |
| Jasmine base | 20 | — |
| Rose base | 10 | — |
| Amyl cinnamon aldehyde | 20 | — |
| Hedione ® (a) | 16 | — |
| Cyclopenta decanolide | 15 | — |
| Galaxolide ® (b) | 10 | — |
| Lyral ® (b) | 4 | — |
| Helional | 5 | — |
| Huminol 1% ® (c) | 2 | — |
| Tabanon 10% ® (c) | 2 | — |
| Parmanyl ® (c) | 2 | — |
| Compound 7a/b/c | 200 | — |
| DPG | — | 200 |
| | 700 | 700 |

(a) Firmenich
(b) IFF
(c) DRAGOCO

EXAMPLE 19

Second use example

Perfume oil for a masculine fine fragrance. The perfume oil of the given formula has a distinct fresh-herby character with citric-green aspects. The addition of 10 parts 7a/b/c results in a very desired harmonisation whilst at the same time emphasising the exciting woody aspects. Alternative additions of 6a/b/c also results in a desired rounding, while the dry-woody aspects are emphasised.

| | | |
|---|---|---|
| Bergamot Oil Italian | 80 | — |
| Dihydromyrcenol | 20 | — |
| Geranium oil BB | 10 | — |
| Linalool | 30 | — |
| Linalyl acetate | 60 | — |
| Lavendula oil French | 30 | — |
| Isogalbanate | 10 | — |
| Isodamascon 10% | 3 | — |
| Cyclogalbanate | 20 | — |
| Brahmanol F | 5 | — |
| Precyclemone B | 5 | — |
| Ambroxane | 20 | — |
| Hedione | 100 | — |
| Anise aldehyde 10% | 7 | — |
| Coumarin | 20 | — |
| Lime oil Tahiti | 40 | — |
| Compounds 7a/7b/7c | 100 | — |
| DPG | — | 100 |
| | 740 | 740 |

(a) Firmenich
(b) IFF
(c) DRAGOCO

In both cases, the addition of isolongifolanyl acetals resulted in an improved fixation of the main notes.

We claim:

1. Isolongifolanol derivatives of the general formula A, in which the wavy lines mean α or β configuration and $R_1$ is hydrogen or methyl and $R_2$ is methyl, ethyl or propyl:

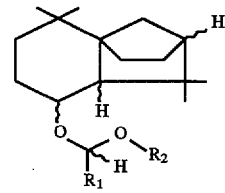

2. Process for production of compounds of the general formula A, in which the wavy lines mean α or β configuration and $R_1$ is hydrogen or methyl and $R_2$ is methyl, ethyl or propyl:

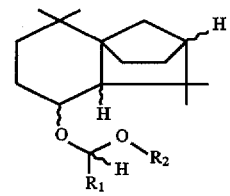

said process comprising:
(a) obtaining isolongifolene from longifolen,
(b) oxidising the isolongifolene obtained from longifolen in step (a) to isolongifolane,
(c) equilibrating with base extraction and/or reducing the isolongifoane produced in step (b) to isolongifolan-3-ol, and
(d) reacting the isolongifolan-3-ol produced in step (c) with a symmetric acetal of the formula $R_2$—OCHR$_1$—O—$R_2$, in which $R_1$ is hydrogen or methyl and $R_2$ is methyl, ethyl or propyl.

3. A process for imparting or enhancing an olfactory property to a composition of matter, said process comprising adding an ioslongifolanol derivative to said composition of matter, wherein said ioslongifolanol derivative is represented by formula A, in which the wavy lines mean α or β configuration and $R_1$ means hydrogen or methyl and $R_2$ means methyl, ethyl or propyl groups:

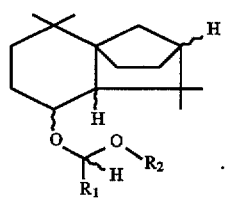

4. A process as in claim 3, wherein said composition of matter is a perfume oil.

5. A process as in claim 3, wherein said composition of matter is a perfume.

6. A process as in claim 3, wherein said composition of matter is a cosmetic composition.

* * * * *